(12) United States Patent
Trainer et al.

(10) Patent No.: US 12,005,199 B2
(45) Date of Patent: Jun. 11, 2024

(54) CATHETER ADAPTER PORT VALVE

(71) Applicant: Becton, Dickinson and Company, Franklin Lakes, NJ (US)

(72) Inventors: Lawrence J. Trainer, Murray, UT (US); S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 155 days.

(21) Appl. No.: 17/718,594

(22) Filed: Apr. 12, 2022

(65) Prior Publication Data

US 2022/0233817 A1    Jul. 28, 2022

Related U.S. Application Data

(63) Continuation of application No. 15/644,467, filed on Jul. 7, 2017, now Pat. No. 11,324,922, which is a continuation of application No. 13/417,525, filed on Mar. 12, 2012, now Pat. No. 9,737,686.

(51) Int. Cl.
*A61M 25/00* (2006.01)
*A61M 25/06* (2006.01)
*A61M 39/02* (2006.01)
*A61M 39/06* (2006.01)

(52) U.S. Cl.
CPC .... *A61M 25/0097* (2013.01); *A61M 25/0606* (2013.01); *A61M 39/06* (2013.01); *A61M 39/0693* (2013.01); *A61M 39/02* (2013.01); *A61M 39/0606* (2013.01); *A61M 2039/062* (2013.01)

(58) Field of Classification Search
CPC ........ A61B 17/3498; A61B 2017/3464; A61B 17/3423; A61B 1/018; A61M 25/02; A61M 2025/0266; A61M 5/158; A61M 2025/024; A61M 2025/0253; A61M 2005/1586; A61M 39/26; A61M 39/02; A61M 39/045; A61M 39/0693; A61M 2039/062; A61M 2039/0633
See application file for complete search history.

(56) References Cited

U.S. PATENT DOCUMENTS

| | | | | |
|---|---|---|---|---|
| 4,063,555 A | * | 12/1977 | Ulinder | A61M 39/02 137/853 |
| 4,106,491 A | * | 8/1978 | Guerra | A61B 5/150519 604/167.03 |
| 4,432,766 A | * | 2/1984 | Bellotti | A61M 39/16 604/905 |
| 4,666,429 A | * | 5/1987 | Stone | A61M 5/1408 604/83 |
| 4,944,728 A | * | 7/1990 | Carrell | A61M 25/0606 604/110 |
| 5,147,333 A | * | 9/1992 | Raines | A61M 39/02 251/149.6 |
| 5,261,895 A | * | 11/1993 | Kablik | A61B 17/3498 604/167.03 |
| 5,360,413 A | * | 11/1994 | Leason | A61M 39/26 604/249 |

(Continued)

*Primary Examiner* — Scott J Medway
(74) *Attorney, Agent, or Firm* — Kirton McConkie; Whitney Blair; Kevin Stinger

(57) ABSTRACT

A catheter assembly is disclosed that includes a catheter adapter having a port disposed on its sidewall. A valve is coupled to the port to seal the opening in the port.

10 Claims, 7 Drawing Sheets

(56) References Cited

U.S. PATENT DOCUMENTS

| | | | | |
|---|---|---|---|---|
| 5,512,043 | A * | 4/1996 | Verkaart | A61M 39/02 137/853 |
| 5,628,306 | A * | 5/1997 | Kee | A61M 16/0463 128/207.14 |
| 5,657,963 | A * | 8/1997 | Hinchliffe | A61M 39/06 604/167.01 |
| 5,676,657 | A * | 10/1997 | Yoon | A61B 17/3462 604/167.03 |
| 6,077,244 | A * | 6/2000 | Botich | A61M 25/0631 604/110 |
| 6,481,462 | B2 * | 11/2002 | Fillmore | A61F 5/4405 251/7 |
| 7,326,188 | B1 * | 2/2008 | Russell | A61M 39/24 604/248 |
| 7,617,837 | B2 * | 11/2009 | Wilson | A61B 5/0215 137/112 |
| 9,597,483 | B2 * | 3/2017 | King | A61M 39/24 |
| 9,814,866 | B1 * | 11/2017 | Goswami | A61M 27/00 |
| 2004/0068239 | A1 * | 4/2004 | Utterberg | A61M 5/16813 604/533 |

* cited by examiner

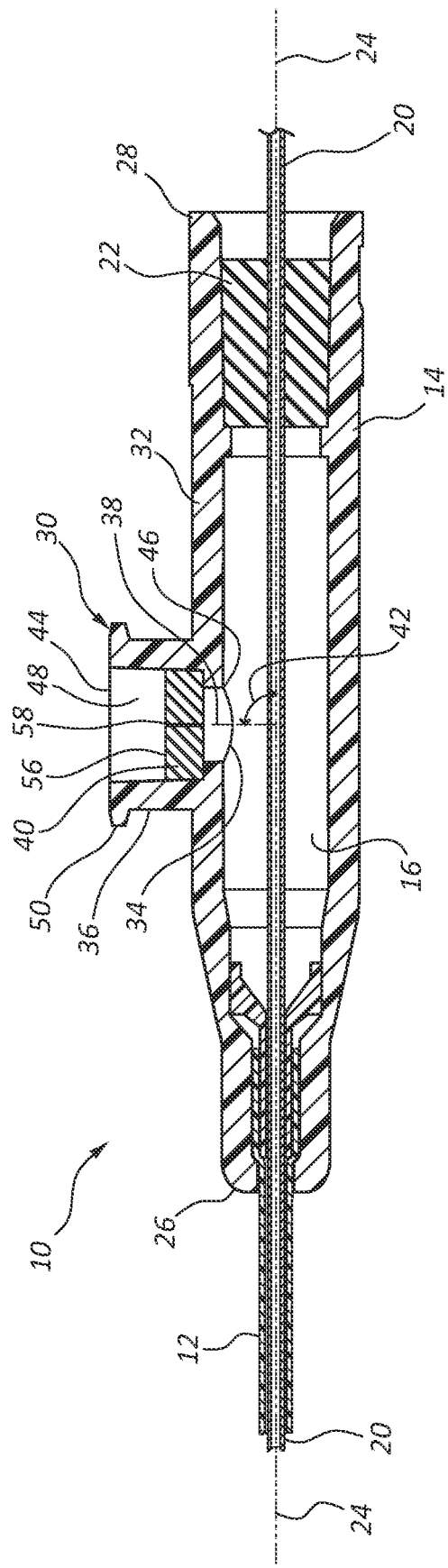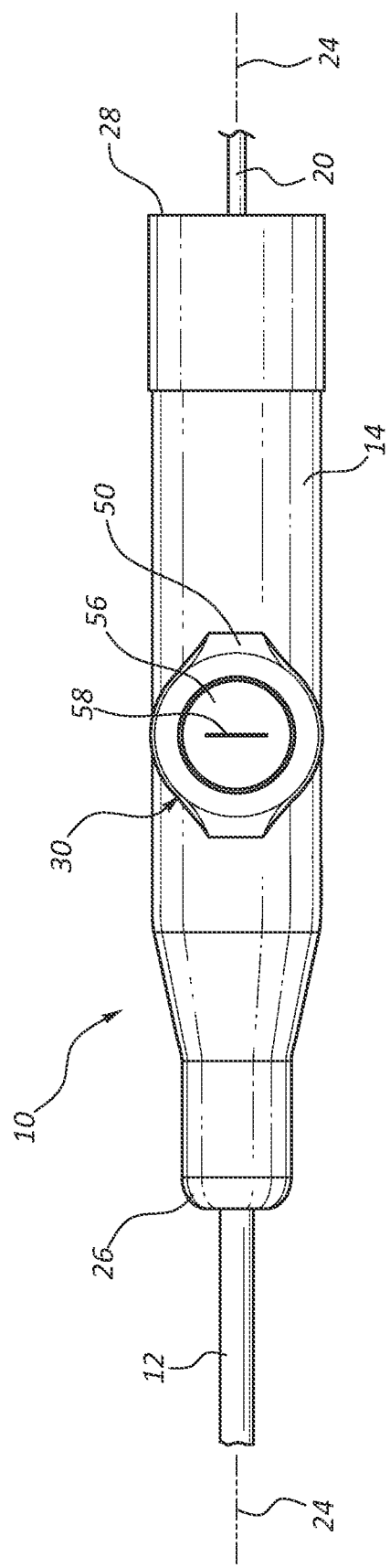
FIG. 1
FIG. 2

CATHETER ADAPTER PORT VALVE

RELATED APPLICATION

This application is a continuation of U.S. patent application Ser. No. 15/644,467, filed on Jul. 7, 2017, entitled CATHETER ADAPTER PORT VALVE, which is a continuation of U.S. patent application Ser. No. 13/417,525, filed on Mar. 12, 2012, entitled CATHETER ADAPTER PORT VALVE, which are incorporated herein in their entirety.

BACKGROUND OF THE INVENTION

The present invention relates to port valves used in catheter assemblies. In medicine, catheter assemblies are used to place a catheter properly into the vascular system of a patient. Once in place, catheters such as intravenous (or "IV") catheters may be used to infuse fluids including normal saline, medicinal compounds, and/or nutritional compositions into a patient in need of such treatment. Catheters additionally enable the removal of fluids from the circulatory system and monitoring of conditions within the vascular system of the patient.

One type of commonly used catheter is a peripheral intravenous catheter. These short, indwelling intravenous catheters are often used to provide an entry route for medications, fluid for hydration, and in some cases, for parenteral feeding, into a patient. Such catheters are generally short in length, ranging from about one-half to about three inches in length, and are generally made of flexible biocompatible materials. Peripheral intravenous catheters are often provided as "over-the-needle" catheters mounted over an introducer needle with a sharp distal tip. A portion of the catheter including at least the distal tip of the catheter securely grips the outside of the needle to prevent catheter peelback during insertion of the catheter into the circulatory system of the patient. Although several techniques for placing such catheters are practiced in the art, many generally include the step of inserting at least a portion of the needle into the target vessel and then sliding the catheter over the needle into place.

Once placement of the needle has been confirmed, the medical personnel may remove the needle, leaving the catheter in place. A septum within the catheter adapter can prevent the outflow of fluid during and following removal of the introducer needle. These septum structures are generally elastomeric and are designed to closely conform to the shape of a needle during storage and use to prevent leaking, then to seal upon removal of the needle. However, if the needle is left within the septum for long periods, the septum may not completely seal after the needle is removed, having conformed, in part, to the shape of the withdrawn needle. An incompletely sealed septum can increase the risk of blood exposure to medical personnel, since blood may flow through the small opening in the slit of the septum. It would thus be an improvement in the art to provide a catheter assembly with more reliable sealing functionality. Such a catheter assembly is disclosed herein.

SUMMARY OF THE INVENTION

The present invention has been developed in response to problems and needs in the art that have not yet been fully resolved by currently available catheter assemblies. Thus, these catheter assemblies are developed to include a valve that is located on a port of a catheter adapter. Placing the valve on the port can avoid the problems involved when a valve is in the path of an introducer needle. This valve can further provide the ability to infuse and withdraw fluids through the port.

Accordingly, in some aspects of the invention, a catheter assembly is provided that includes a catheter adapter having an inner lumen. A port in the catheter adapter can form an opening into the inner lumen. A valve can be coupled to the port and which selectively seal the opening of the port. The catheter assembly can also have a catheter tube and a septum within the inner lumen that seals the proximal end of the inner lumen.

Various types of valves can be incorporated into the port to provide medical personnel with the ability to infuse and withdraw fluids through the port. Non-limiting examples of valves include an elastomeric septum, a ball valve, and an iris valve. The valve can be a one-way valve or a two-way valve. The valve can be located on a removable luer access connector that can be connected and disconnected from the port. Alternatively, the valve can be located on a luer access connector that is fixedly connected to the port. The valve can be a luer access valve that accommodates the insertion of a luer device, such as those commonly used in the medical industry. Moreover, a body portion of the port can include luer threads that can secure a luer device to the catheter adapter. In some configurations, the port can be disposed at an angle relative to the longitudinal axis of the catheter in order to modify the direction at which fluids are infused into the inner lumen. This angle can be between about 15° to about 90°.

Additionally, the valve on a port can provide a number of benefits when used with blood control-type catheter assemblies. Blood control-type catheter assemblies can have an internal blood control valve that may remain permanently open after it is activated by the insertion of a luer. In these instances, the valve can provide medical personnel with an additional point of connection that has a limited risk of blood exposure. Accordingly, in some implementations of the invention, the valve on the port is utilized with a catheter assembly having an internal blood control valve. The blood control valve may include a blood control septum located within the inner lumen of the catheter adapter. A septum activator may also be located within the inner lumen at a location that is behind the blood control septum. When a separate luer device is inserted into the proximal end of the catheter adapter, the septum activator is advanced forward through the blood control septum, activating the blood control septum.

In some aspects of the invention, a button that extends outwardly from a sidewall of the catheter adapter can activate and deactivate the blood control septum. The button can be connected to the septum activator and configured to move the septum activator distally through the septum when the button is pressed. In some implementations, the button is configured to be pressed inwardly towards the inner lumen, and a translating mechanism translates the inward movement of the button to a distal movement of the septum activator.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 1 illustrates a cross-sectioned, side view of a representative catheter assembly having a port and a valve.

FIG. 2 illustrates a perspective, top view of the catheter assembly of FIG. 1.

DETAILED DESCRIPTION OF THE INVENTION

Figure 4:
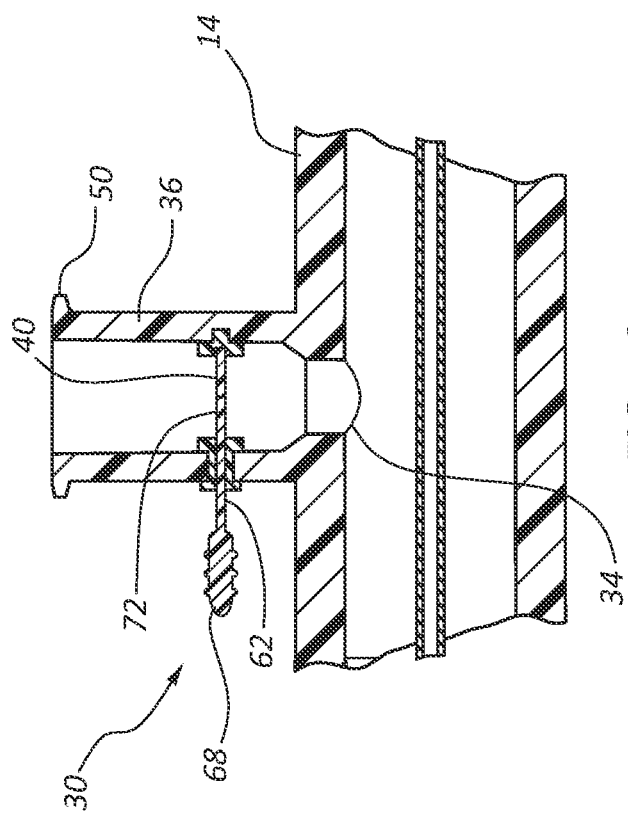
FIG. 4 illustrates a partial cross-sectioned view of a representative iris valve on a port.

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

As used herein, the term "proximal", "behind", "top", "up", or "upwardly" refers to a location on the device that is closest to the clinician using the device and farthest from the patient in connection with whom the device is used when the device is used in its normal operation. Conversely, the term "distal", "forward", "bottom", "down", or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

FIG. 1 illustrates a cross-sectioned view of one embodiment of a catheter assembly 10. As shown, the catheter assembly 10 generally includes a catheter 12 coupled to the distal end 26 of a catheter adapter 14. The catheter 12 and the catheter adapter 14 are integrally coupled such that an inner lumen 16 of the catheter adapter 14 extends into the catheter 12. The catheter 12 generally includes a biocompatible material that is made of a flexible or a semi-flexible polymer. The catheter 12 may be used in combination with a rigid introducer needle 20, as shown, to enable insertion of the catheter 12 into a patient. It is contemplated that other types of implantable catheter assemblies may also be used in combination with the present invention.

After the introducer needle 20 is removed from the catheter 12 and catheter adapter 14, fluids may be infused into the patient. These fluids can include normal saline, medicinal compounds, and/or nutritional compositions (including total parenteral nutrition, or "TPN"). Fluids, such as blood samples, can also be removed from the circulatory system of the patient through the catheter 12 for monitoring of conditions within the vascular system of the patient.

In some embodiments, a needle septum 22 is disposed within the catheter adapter 14 to prevent the outflow of fluid during and following removal of the introducer needle 20. The needle septum 22 can be elastomeric and be designed to closely conform to the shape of an introducer needle 20 to prevent leaking. The needle septum 22 can also seal upon removal of the needle due to axial compression forces on the needle septum 22 that induces it to close.

In some instances, fluids may be infused and withdrawn from the catheter 12 through a port 30 in a sidewall 32 of the catheter adapter 14. The port 30 can form an opening 34 extending through a sidewall 32 of the catheter adapter 14. The sidewall 32 can be any wall of the catheter adapter 14 that extends substantially longitudinally (in relation to the longitudinal axis 24) along the catheter adapter 14. A port 30 can be a side port or a top port. The port 30 can form a fluid path from the external environment into the inner lumen 16 of the catheter adapter 14.

To prevent contamination from entering the catheter adapter 14 through the port 30, a valve 40 can be coupled to the port 30 that provides selective access through the port 30. In some embodiments, the valve 40 can be a two-way valve. A two-way valve is a valve 40 that permits fluid flow in two directions through the valve 40 when the valve 40 is open. Non-limiting examples of a two-way valve include a split septum, a ball valve, and an iris valve. Thus, a two-way valve can permit fluid to be introduced into the catheter adapter 14 (a first way) and to be withdrawn from the catheter adapter 14 (a second way). In other embodiments, the valve 40 is a one-way valve, which is a valve 40 that only permits substantial fluid flow in a single direction when the valve 40 is open. A non-limiting example of a one-way valve is a check valve. In some embodiments, no other valves are used to regulate fluid flow through the port 30 other than the valve 40. By thus positioning the valve 40 on a port 30 of a catheter adapter 14, the valve 40 can avoid problems caused when an introducer needle 20 is left within an in-line valve for an extended time.

Figure 6:
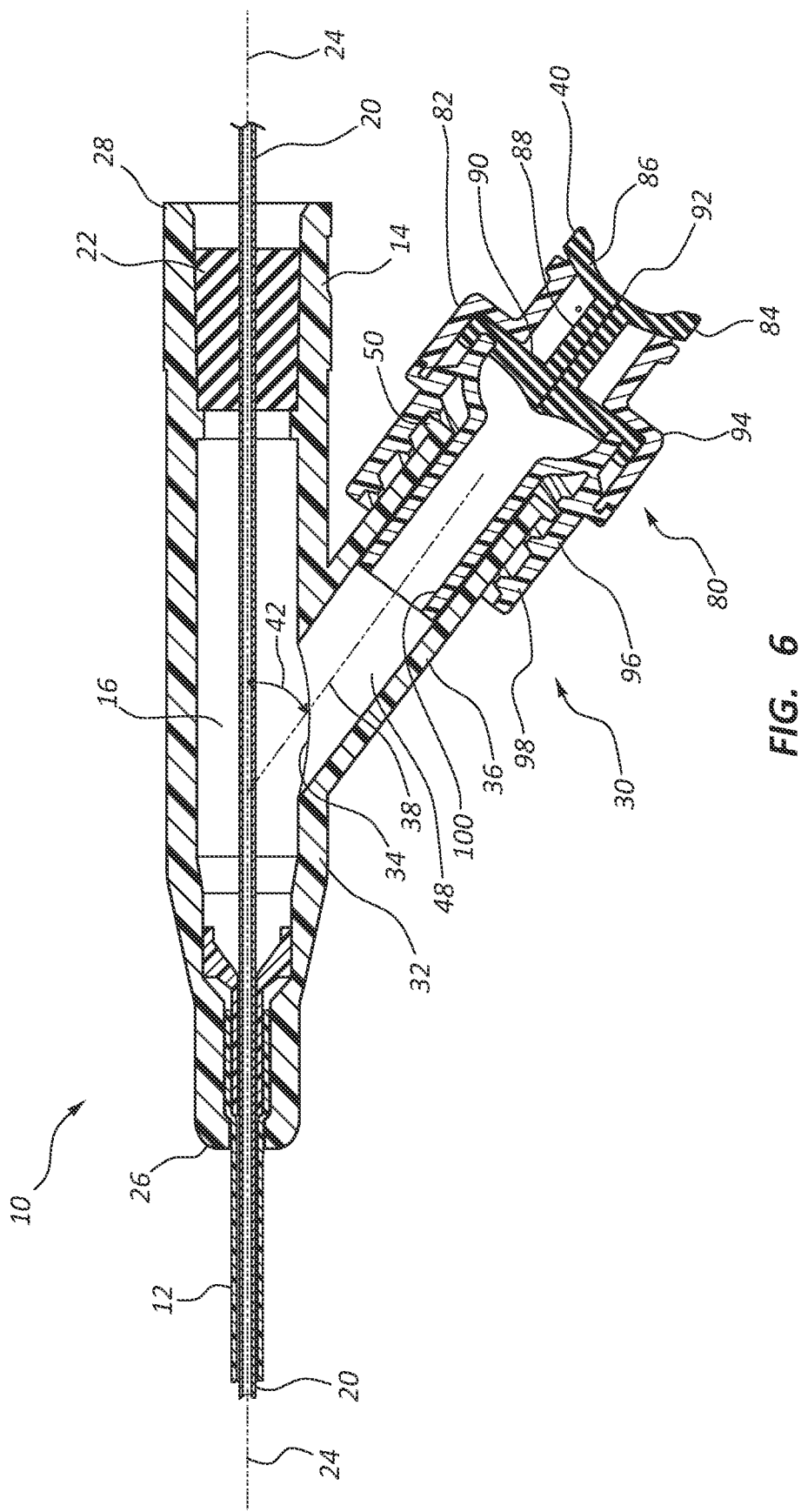
FIG. 6 illustrates a cross-sectioned view of a representative removable valve on a port.

In some configurations, the port 30 can be disposed at an angle 42 relative to the longitudinal axis 24 of the catheter adapter 14. The angle 42 can be measured between the portion of the longitudinal axis 24 extending to the proximal end of the catheter adapter 14 and the central axis 38 of the port 40. For example, the angle 42 of the port 30 of FIG. 1 is about 90° and the angle 42 of the port 30 of FIG. 6 is about 45°. The angle 42 can at least partially control to the direction at which fluids are infused though the port 30. Thus, the angle 42 of the port 30 can be modified to facilitate use, optimize performance, and/or optimize fluid flow within the inner lumen 16. In some embodiments, the angle 42 is between about 15° to about 30°. In other embodiments, the angle 42 is between about 30° to about 45°. In still other embodiments, this angle 42 is between about 45° to about 60°. In yet other embodiments, the angle 42 is between about 60° to about 90°. Accordingly, in some embodiments, the angle 42 is between about 15° to about 90°.

The port 30 can include a port body 36 having one or more integrated body portions, which extend outwardly from the sidewall 32 of the catheter adapter 14. Typical plastic materials such as, for example, polycarbonate, polyethylene, polypropylene and co-polyesters could be used to form the port body 36. The port body 36 can define an inlet 44 and a bore 48 extending between the inlet 44 and the opening 34 of the inner lumen 18. The inlet 44 and at least a portion of bore 48 can be shaped and sized in conformity with at least some of the International Standards Organization (ISO) standards for a female luer connection. This will allow a male luer slip or male luer lock to be connected to port 30.

Figure 9:
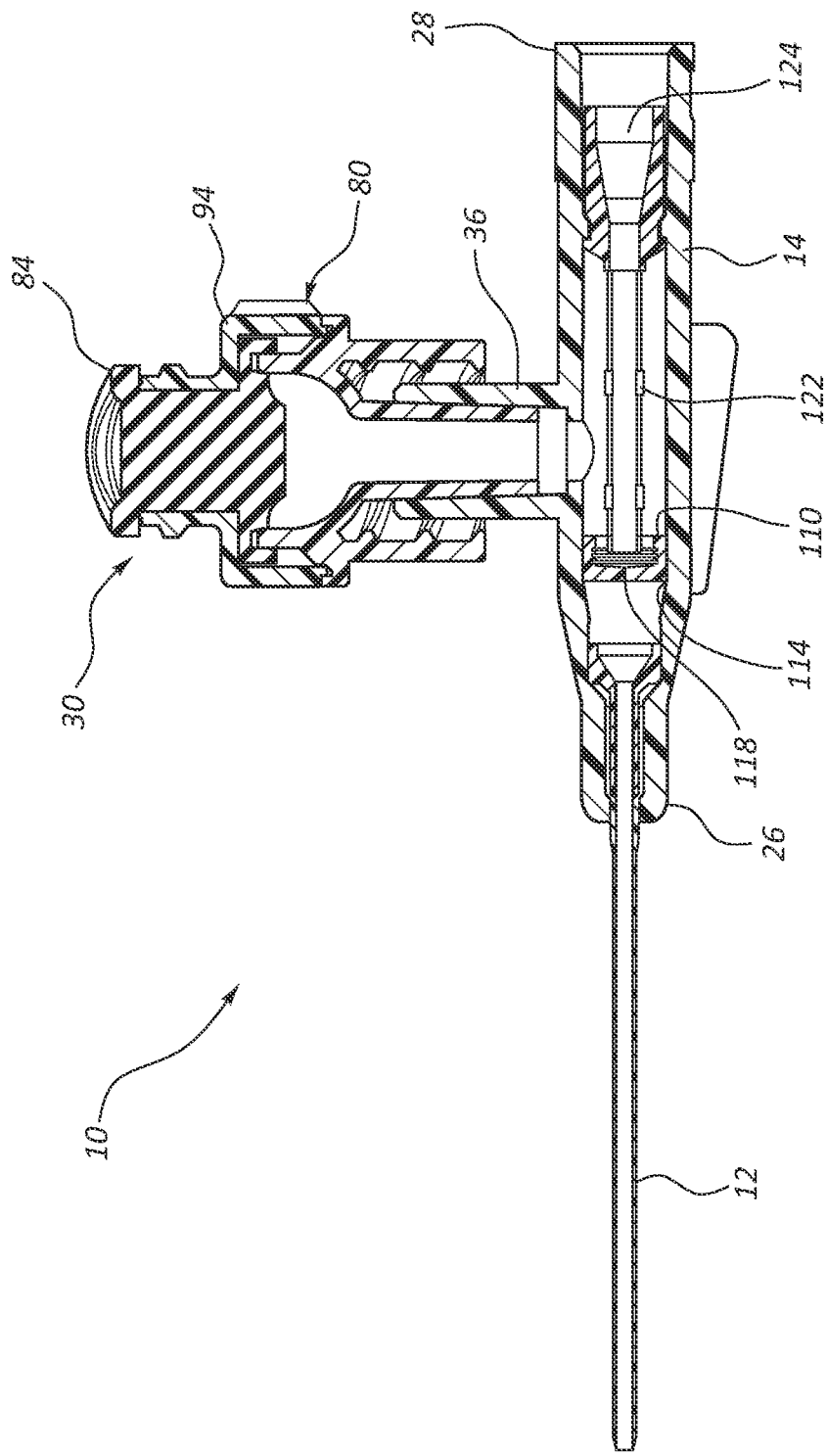
FIG. 9 illustrates a cross-section view of yet another representative catheter assembly having a removable valve on a port.

In various embodiments, the exterior of the port body 36 can include one or more luer threads 50 in any number of thread configurations available to provide and interlock between mating devices. The luer threads 50 can allow another medical device having a male luer lock to be connected to and interlocked with the port 30. Alternatively, as shown in FIG. 9, the port body 36 can also have no luer threads to accommodate luer slip and luer lock connections.

FIGS. 1 through 9 illustrate various types of valves 40 that can be used in accordance with various embodiments of the port 30. These valve types are not presented as an exhaustive set of valve types, and thus it will be understood that other suitable valves 40 can be utilized in port 30. Reference will first be made to the valve 40 of FIG. 1. The valve 40 can include an elastomeric septum 56 that can form a fluid barrier until it deforms to allow fluid flow therethrough. The septum 56 can be located on the inlet 44, within the inlet 44, or within the bore 48 of the port body 36. Materials such as silicone, silicone rubber, or polyisoprene can be used to form septum 56. The septum 56 can be formed as a single piece of elastomeric material that is formed to having various shapes and features. Alternatively, the septum 56 can be a two-piece configuration having a flexible inner material, such as silicon or silicone rubber, and a more rigid outer portion, such as an outer ring. The outer ring can be formed of a plastic or metal or other suitable material. The septum 56 can also include a slit 58. In some configurations, at least a portion of the septum 56 is glued to the port body 36 using one or more adhesives. Additionally or alternatively, in some configurations, at least a portion of the septum 56 is held in place between two or more portions of the port body 36.

FIG. 2 illustrates a perspective top view of the catheter assembly 10 of FIG. 1. As shown, the port 30 can be accessed, with a male luer device (such as the luer access connector 80 of FIG. 6) that is inserted through the slit 58 of the septum 56. The male luer device can be interlocked with the luer threads 50 if the male luer device includes a luer lock. In this manner, a separate access device can be coupled to the catheter adapter 14 through the port 30 to establish fluid communication therethrough. Additionally, a syringe, needle, or other such device can be inserted through the slit 58 of the septum 58 to withdraw fluids therethrough.

Figure 5:
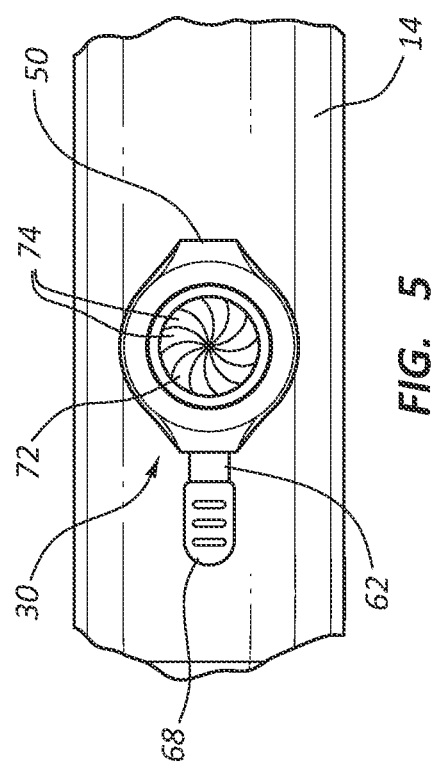
FIG. 5 illustrates a top view of the iris valve of FIG. 4.
Figure 3:
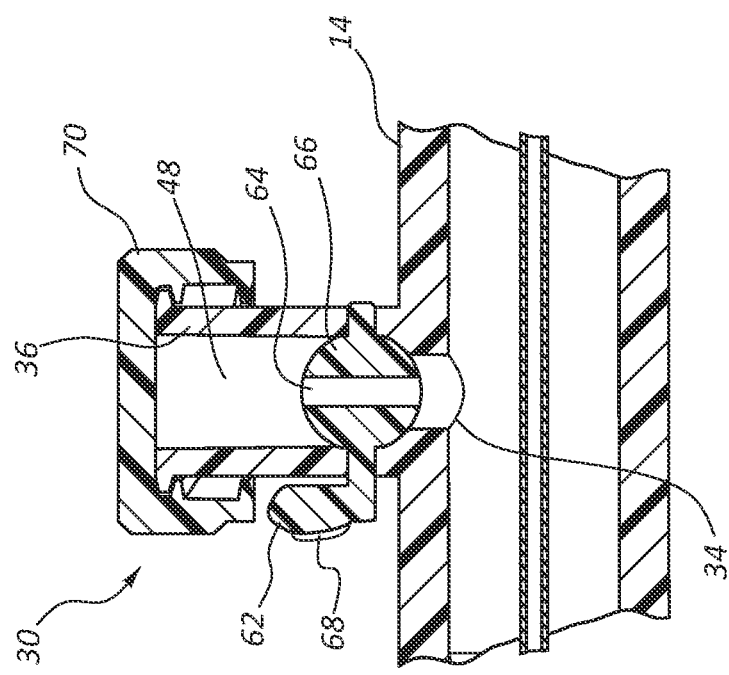
FIG. 3 illustrates a partial cross-sectioned view of a representative ball valve on a port.

FIGS. 3 to 5 will now be referenced. These figures illustrate the use of manually activated valves 40 that can control the flow of fluid through the port 30. Reference will first be made to FIG. 3, which illustrates a ball valve 60 that includes a spherical member 66 disposed within the bore 48 of the port 30. The spherical member 66 can have a hole 64 through the middle so that when the hole 64 is in line with a central axis 38 of the port 30, the ball valve 60 is open. By turning the spherical member 66, such as with an actuator 62, the hole 64 becomes perpendicular to the central axis 38 of the port body 36 and the ball valve 60 is closed. An actuator 62 can be coupled to the spherical member 66 such that as the actuator 62 is turned, the spherical member 66 is moved between the open and the closed positions. In some configuration, as shown, the actuator 62 includes the gripping portion 68 that is shaped and sized to accommodate the fingers of a medical personnel and to provide leverage for turning the actuator 62.

Some embodiments of the ball valve 60 are configure so that the hole 64 through the spherical member 66 is in conformity with at least some of the ISO standards for a female luer connection, as described above. This configuration can permit the insertion of a male luer into the hole 64 of the spherical member 66 as the male luer is inserted into the port 30. Additionally, as shown, a cap 70 can be removably coupled to the inlet 44 of the port 30. The cap 70 can cover the inlet 44 and prevent contamination from entering therein.

FIGS. 4 and 5 illustrate another manually activated valve 40, an iris valve. FIG. 4 illustrates a cross-sectioned view of the iris valve 72. The iris valve 72 can generally includes a series of plates 74 that can fold in on each other and expand out to open and close the port 30. When actuated, this series of plates 74 can open by degrees to provide a variable sized opening through the iris valve 72. FIG. 5 illustrates a top perspective view of the iris valve 72. As shown, the iris valve 72 is in a closed position with the series of plates 72 forming a barrier across the port 30 that seals the opening 34 into the inner lumen 16 of the catheter adapter 14. An actuator 62 can be coupled to the iris valve 72 such that as the actuator 62 is moved, the iris valve 72 is moved between the open and the closed positions. In some configuration, as shown, the actuator 62 includes the gripping portion 68 that is shaped and sized to accommodate the fingers of a medical personnel and to provide leverage for turning the actuator 62.

Reference will now be made to FIG. 6, which illustrates a port 30 with a central axis 38 disposed at an angle 42 of approximately 45° relative to the longitudinal axis 24 of the catheter adapter 14. As shown, in some embodiments, the port 30 can be coupled to a removable valve 40. The removable valve 40 can be selectively coupled to the port body 36, such as, via the luer threads 50. For instance, the removable valve 40 can be coupled to a removable luer access connector 80. A non-limiting example of such a luer access connector 80 is described in United States Published Patent Application No. 2003/0109853, filed on Dec. 7, 2001, entitled, "Needleless luer access connector," which is herein incorporated by reference in its entirety. Other such luer access connectors 80 can also be used. As shown, some embodiments of a luer access connector 80 can include a housing 82 having a top housing portion 94 and bottom housing portion 96. A septum 84 can be located in top housing portion 94 of the luer access connector 80 to control fluid flow therethrough. The septum 84 can have a top portion 86, a medial portion 88, and a bottom portion 90. The bottom portion 21 of the septum 84 can be disposed and/or held in tension between the top housing portion 94 and bottom housing portion 96. Additionally, a slit 92 can be formed in septum 84 which extends longitudinally through proximal portion 86, medial portion 88, and distal portion 90 of the septum 84.

The bottom housing portion 96 of the luer access connector 80 can have an outlet 100 that is sized and configured as a male luer taper that complies with the ISO standards for a male luer taper and which thus can be inserted into the bore 48 of the port 30. Moreover, the bottom housing portion 96 can include a luer lock collar 98 formed about the outlet 100 to selectively lock the luer access connector 80 to the luer threads 50 of the port body 36.

Figure 7:
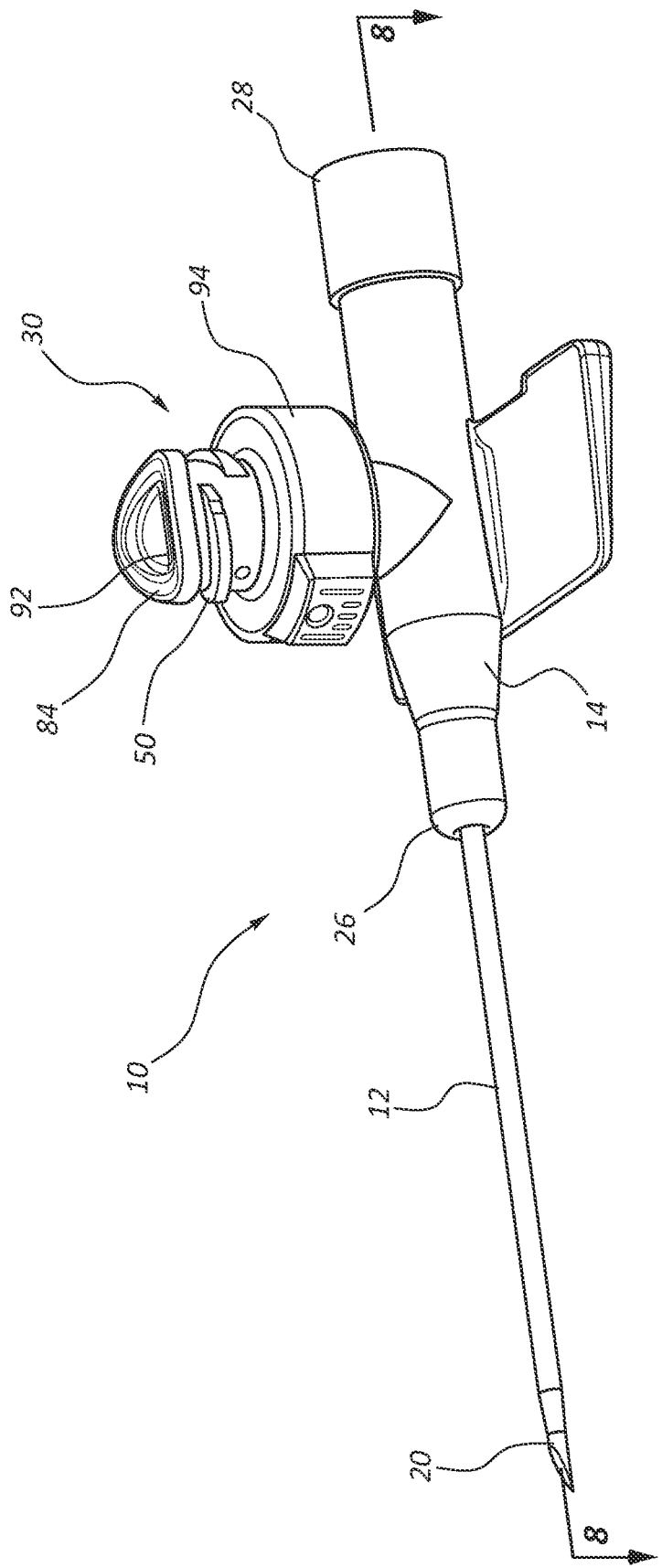
FIG. 7 illustrates a perspective view of another representative catheter assembly having a valve on a port and a needle extending through the catheter assembly.

Turning now to FIG. 7, in some embodiments, the top housing portion 94 of the luer access connector 80 is connected directly and/or fixedly to the port body 36. This configuration can reduce the overall port size and number of require parts included in the port 30.

Figure 8:
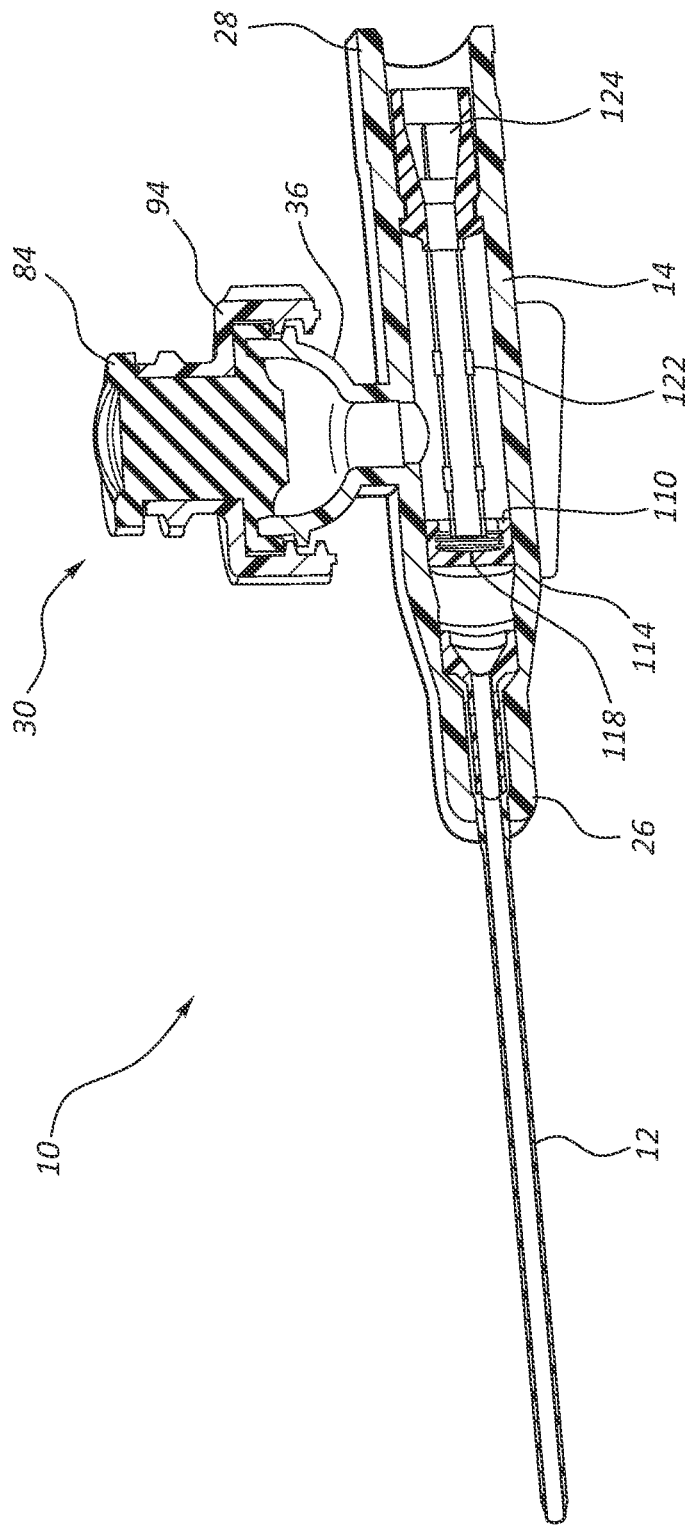
FIG. 8 illustrates a cross-sectioned view of the catheter assembly of FIG. 7 taken along line 8-8 of FIG. 7 with the needle removed.

FIG. 8 depicts a cross-sectioned view of the catheter assembly of FIG. 7 taken along line 8-8 of FIG. 7. As shown, in embodiments where top housing portion 94 of a valve housing 82 is directly connected to the port body 36, the bottom portion 90 of the septum 84 can be held in tension between the top housing portion 94 and the port body 36. Moreover, to secure this connection, the top housing portion 94 and the port body 36 can be bonded together to prevent contamination of the port 30. Any standard bonding technique, such as chemical adhesive or ultrasonic welding can be used to bond top housing portion 94 of the housing to port body 36. In addition, as shown, the shape and size of the port body 36 can be configured to accommodate the movement of the septum 84.

As further shown in FIG. 8, in some embodiments, a port 30 and the valve 40 are used with a blood control-type catheter assembly 10. Blood control-type catheter assemblies 10 generally includes a blood control septum 110 disposed within the inner lumen 16 of the catheter assembly 10. The blood control septum 110 can open by a septum activator 112 when a luer device (not shown) is inserted into the proximal end 28 of the catheter adapter 14. The luer device can advance the septum activator 112 distally through the blood control septum 110 to form an open fluid path therethrough. A representative blood control-type catheter assembly is disclosed in United States Published Patent Application No. 2011/0046570, entitled "Systems and methods for providing a flushable catheter assembly," filed Aug. 20, 2009, which is herein incorporated by reference in its entirety.

A valve in the port 30 can provide a number of benefits to the blood control-type catheter assemblies 10. For instance, a blood control septum 110 may remain open after the septum activator 112 is inserted through the blood control septum 110. This blood control septum 110 may remain open, even after the male luer that advanced the septum activator 122 is removed. In this open state, fluids can flow out the catheter adapter 14 and be exposed to medical personnel. However, using the valve on the port 30, medical personnel can access the inner lumen 16 of the catheter adapter 14 without being exposed to the patient's blood.

Specific reference will now be made to the components of the blood control-type catheter assembly 10 depicted in FIG. 8. As shown, a catheter assembly 14 can have a blood control septum 110 located within the inner lumen 16 of the catheter adapter 14. A septum activator 112 can be located within the inner lumen 16 at a location that is behind the blood control septum 110. The blood control septum 110 can generally comprises a flexible or semi-flexible polymer plug. The blood control septum 110 can have an outer diameter that is configured to compatibly seat within a groove or channel 114 formed on an inner surface 116 of the catheter adapter 14. Alternatively, a groove or channel can be formed in the outer surface of the blood control septum 110, which interlocks with one or more features on the inner surface 116 of the catheter adapter 14. In some embodiments, the blood control septum 110 is barrel shaped, while in other configurations, the blood control septum 110 is substantially cylindrical or disk shaped. The blood control septum 110 can be elastomeric and include one or more slits 118 through which the septum activator 112 can be inserted.

The septum activator 112 can be a probe-like structure that is primarily housed behind the septum 110 within the inner lumen 16 of the catheter adapter 14. The septum activator 112 generally comprises a tubular body 122 that is rigid or semi-rigid. The tubular body 122 further comprises an inner lumen 124 for facilitating flow of a fluid and/or liquid through the septum activator 112. The distal end of the tubular body 122 can be shaped and sized to compatibly enter within the one or more slits 118 of the septum 110.

Referring now to FIG. 9, in some instances, as shown, the exterior of the port body 36 may have no luer threads. This can allow for a luer access connector 80 or another separate luer device having a male luer slip to be connected to the port body 36. This type of port 30 can thus enable a wide variety of devices to be connected therein. Furthermore, in some instances, a septum 56, such as that shown in FIG. 1, can be included within the port 30 to avoid blood exposure when the separate luer device is removed from the port 30.

Figure 10:
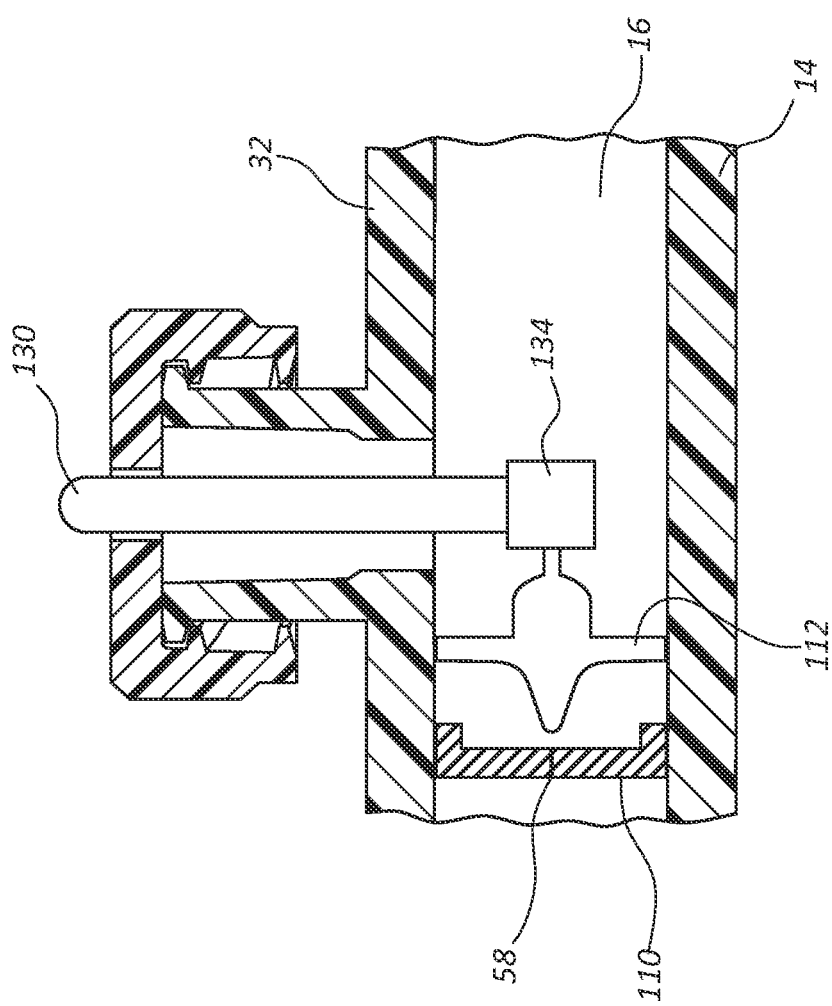
FIG. 10 illustrates a partial cross-sectioned view of a representative push-button mechanism for actuating a blood control septum within a catheter assembly.

Turning now to FIG. 10, in some embodiments, the septum activator 112 of a blood control-type catheter assembly 10 can be activated and/or deactivated by pressing a button 130 on a port 30. The button 130 can enable medical personnel to manually activate and deactivate the septum 110 as needed. In operation, the septum activator 112 can be advanced distally through the septum 110 when the button 130 is pressed a first time, and withdrawn from the septum 110 when the button 130 is pressed a second time. In some configurations, the button 130 is coupled to the sidewall 32 and extends outwardly from the catheter adapter 14. Moreover, the button 130 can be coupled directly to the septum activator 112 or be indirectly coupled thereto via one or more connecting members. For example, the button 130 can be coupled to one or more translating mechanisms 134 that translate the inward movement of the button 130 to distal or proximal movements of the septum activator 112.

From the foregoing it will be understood, that a catheter assembly of the present invention can include a valve that is located on a port of a catheter adapter rather than in-line with the needle path of an introducer needle. This valve on a port can avoid problems caused when a needle is left within septum for an extended period and further provide the ability to infuse and withdraw fluids through the port. This valve can be a two-way valve that facilitates the infusion and withdrawal of fluids to and from the catheter assembly. When used with blood control-type catheter assemblies, the valve can reduce the likelihood of blood contamination when connecting and disconnecting various components to the catheter assembly. Some configurations also include a push-button septum activator that can provide medical personnel with the ability to manually activate and deactivate the blood control valve as needed.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method, comprising:
   pressing a button of an intravenous catheter assembly a first time, wherein the intravenous catheter assembly comprises:
   a catheter adapter having a sidewall extending between a distal end of the catheter adapter and a proximal end of the catheter adapter, wherein the catheter adapter further comprises an inner lumen extending within the sidewall between the distal end and the proximal end;
   an intravenous catheter coupled to the distal end of the catheter adapter, the intravenous catheter having an inner lumen in fluid communication with the inner lumen of the catheter adapter;
   a port disposed on the sidewall of the catheter adapter, the port forming an opening between the inner lumen and an external environment such that the port provides direct access to the inner lumen of the catheter adapter;
   a septum positioned within the inner lumen of the catheter adapter;
   a septum activator positioned within the inner lumen of the catheter adapter, the septum activator configured to be forced through the septum to open a fluid pathway through the inner lumen; and
   the button that extends through the port, wherein when the button is pressed the first time the septum activator is forced through the septum, wherein the button is configured to be pressed inwardly towards the inner lumen of the catheter adapter.

2. The method of claim 1, further comprising pressing the button a second time, wherein when the button is pressed the second time, the septum activator is withdrawn from the septum.

3. The method of claim of claim 1, wherein the button is coupled with one or more translator elements that translate inward movement of the button to a distal movement of the septum activator.

4. The method of claim of claim 3, wherein the one or more translator elements are disposed in the inner lumen of the catheter adapter.

5. The method of claim 1, wherein the button extends through the opening.

6. The method of claim 1, wherein the button extends through the port perpendicular to a longitudinal axis of the inner lumen of the catheter adapter.

7. The method of claim 1, wherein the button protrudes from the port to allow a user to press the button.

8. The method of claim 1, wherein the port includes a first end coupled with the side wall and a second end opposite the first end, wherein the button protrudes from the second end to allow a user to press the button.

9. A method, comprising:
   pressing a button of an intravenous catheter assembly a first time, wherein the intravenous catheter assembly comprises:
   a catheter adapter having a sidewall extending between a distal end and a proximal end and an inner lumen extending within the sidewall between the distal end and the proximal end;
   an intravenous catheter coupled to the distal end of the catheter adapter, the intravenous catheter having an inner lumen in fluid communication with the inner lumen of the catheter adapter;
   a port disposed on the sidewall of the catheter adapter, the port forming an opening between the inner lumen and an external environment such that the port provides direct access to the inner lumen of the catheter adapter;
   a septum positioned within the inner lumen of the catheter adapter;
   a septum activator positioned within the inner lumen of the catheter adapter, the septum activator configured to be forced through the septum to open a fluid pathway through the inner lumen; and
   the button that extends through the port, wherein when the button is pressed the first time the septum activator is forced through the septum, wherein the button is coupled with one or more translator elements that translate the inward movement of the button to a distal movement of the septum activator.

10. The method of claim of 9, wherein the one or more translator elements are disposed in the inner lumen of the catheter adapter.

* * * * *